United States Patent
Saha

(10) Patent No.: US 8,039,676 B2
(45) Date of Patent: Oct. 18, 2011

(54) PROCESS FOR PRODUCING PHOSPHINE OXIDE VITAMIN D PRECURSORS

(75) Inventor: Uttam Saha, Ontario (CA)

(73) Assignee: Cytochroma Inc., Markham (CA)

( * ) Notice: Subject to any disclaimer, the term of this patent is extended or adjusted under 35 U.S.C. 154(b) by 63 days.

(21) Appl. No.: 12/128,992

(22) Filed: May 29, 2008

(65) Prior Publication Data

US 2008/0300427 A1 Dec. 4, 2008

Related U.S. Application Data

(60) Provisional application No. 60/940,866, filed on May 30, 2007.

(51) Int. Cl.
C07F 9/53 (2006.01)
(52) U.S. Cl. ........................................................ 568/15
(58) Field of Classification Search .................... 568/15, 568/8; 552/653; 514/167
See application file for complete search history.

(56) References Cited

U.S. PATENT DOCUMENTS

| 3,992,432 A | 11/1976 | Napier et al. |
| 4,880,894 A | 11/1989 | Sunkel et al. |
| 6,331,642 B1 | 12/2001 | Batcho et al. |
| 6,603,030 B1 * | 8/2003 | Kabat ........................... 552/653 |

FOREIGN PATENT DOCUMENTS

| CA | 2306000 | | 10/2000 |
| EP | 0516410 | | 12/1992 |
| EP | 0 808 833 A2 | | 11/1997 |
| WO | WO 2007022433 | * | 2/2007 |
| WO | WO-2008/043857 | | 4/2008 |

OTHER PUBLICATIONS

Khachatryan et al., {Interphase Catalysis in Synthesis of Unsaturated Phosphine Oxides, [Mezhfaznyi kataliz v sinteze nenasyshchennykh fosfinoksidov]; 1999, 52(1-2), 77-84}.*
R.A. Khachatrya, et al., "Phase-Transfer Catalysis Applied to the Synthesis of Unsaturated Phosphine Oxides", Armenian Chemical Journal, vol. 38, No. 6, pp. 377-382, 1985. (English language translation also included).
Li, et al., "What are the pKa Values of Organophosphorus Compounds?", Tetrahedron, vol. 62, pp. 4453-4462, 2006.
Lebel, et al., "Alkylation of Phosphine Boranes by Phase-Transfer Catalysis", Organic Letters, vol. 5, No. 13, pp. 2347-2349 (2003).
Starks, CM, et al., "Phase-Transfer Catalysis, Fundamentals, Applications and Industrial Perspectives", 1994 Chapman and Hall, Inc.; Chapters 1-4, 6 and 7.
Daniewski, AR, et al.; "Improved Preparation of A-Ring Phosphine Oxides for the Synthesis of Vitamin D Analogs", Synthetic Communications 2002; 32(19), 3031-3039, Scheme 2.
Mascarenas, JL, et al.; "Studies on the Synthesis of Side-Chain Hydroxylated Metabolites of Vitamin D. 3. Synthesis of 25-Ketovitamin D3 and 25-Hydroxyvitamin D3 ", J. Org. Chem. 1986, 51, 1269-1272.
Kutner, A. et al.; "Synthesis of Retiferol RAD1 and RAD2, the Lead Representatives of a New Class of des-CD Analogs of Cholecalciferol", Bioorganic Chemistry 1995, 23, 22-32, Schemes 4-5; p. 30-31.
Posner, GH, et al.; "Novel A-Ring Analogs of the Hormone 1α, 25-dihydroxyvitamin D3: Synthesis and Preliminary Biological Evaluation", Bioorg. Med. Chem. 2005, 13, 2959-2966.
Posner, GH, et al.; "Difluoromethyl Analogs of the Natural Hormone 1 α, 25-dihydroxyvitamin D3: Design, Synthesis and Preliminary Biological Evaluation", J. Steroid Biochem. Mol. Biol. 2007, 103, 213-221, Scheme 1; p. 217-218.
International Search Report and Written Opinion from counterpart PCT application No. PCT/IB2008/001321 dated Oct. 21, 2008.

* cited by examiner

Primary Examiner — Kamal Saeed
Assistant Examiner — Nyeemah A Grazier
(74) Attorney, Agent, or Firm — Marshall, Gerstein & Borun LLP

(57) ABSTRACT

A process for producing a compound of the formula:

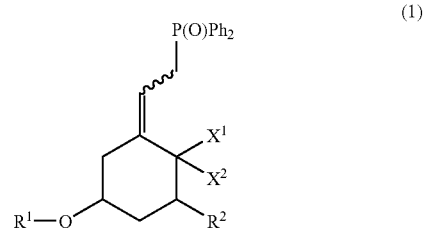

(1)

including reacting of a compound of the formula:

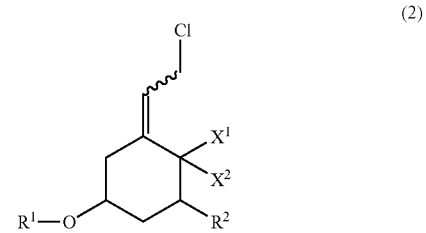

(2)

with diphenyl phosphine oxide using a binary phase reaction mixture including diphenyl phosphine oxide in an organic solvent, a basic aqueous solution, and a phase transfer catalyst, to obtain the compound of formula 1, wherein Ph is phenyl, $X^1$ and $X^2$ are both hydrogen or $X^1$ and $X^2$ taken together are $CH_2$, $R^1$ is a protecting group, $R^2$ is fluorine, hydrogen, or $OR^3$, wherein $R^3$ is a protecting group, and the squiggly line represents a bond that results in the adjacent double bond being in either the E or Z configuration, is disclosed.

19 Claims, No Drawings

PROCESS FOR PRODUCING PHOSPHINE OXIDE VITAMIN D PRECURSORS

CROSS REFERENCE TO RELATED APPLICATIONS

The benefit under 35 U.S.C. §119(e) of U.S. Provisional Application No. 60/940,866, filed May 30, 2007, is hereby claimed and the entire disclosure thereof is hereby incorporated by reference herein.

BACKGROUND

1. Field of the Disclosure

The disclosure relates generally to phosphine oxide Vitamin D precursors. More particularly, the disclosure relates to a process for preparing phosphine oxide Vitamin D precursors using an aqueous base and phase transfer catalyst for deprotonation, instead of using a metal hydride base.

2. Brief Description of Related Technology

Vitamin D analogs, such as 1α-fluoro-25-hydroxy-16-23E-diene-26,27-bishomo-20-epi-cholecalciferol, 25-dihydroxy-16-ene-23-yne-26,27-bishomo-19-nor-20-epicholecalciferol, 1α,25-dihydroxy-18-norvitamin $D_3$, 1α,25-dihydroxy-18,19-dinorvitamin $D_3$, 1α-fluoro-25-hydroxycholecalciferol, and 1α-fluoro-25-hydroxyergocalciferol, are known to have pharmaceutical activity and are useful for treating various conditions, such as psoriasis and neoplastic disease.

A key phosphine oxide compound of formula 1 below is used in the efficient synthesis of such vitamin D analogs and provides the A-ring of the vitamin. Certain species of the compound of formula 1 are known to be valuable intermediates in the synthesis of the mentioned pharmacologically active vitamin D analogs (see, for example, EP Publication No. 0 808 833). The remaining species of the compound of formula 1 can be modified to be useful in the above processes or can be used for producing other vitamin D analogs.

SUMMARY

The invention provides a process for producing a compound of the formula:

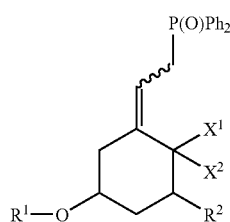

(1)

wherein Ph is phenyl, $X^1$ and $X^2$ are both hydrogen or $X^1$ and $X^2$ taken together are $CH_2$, $R^1$ is a protecting group, $R^2$ is fluorine, hydrogen, or $OR^3$, wherein $R^3$ is a protecting group, and the squiggly line represents a bond that results in the adjacent double bond being in either the E or Z configuration. This process comprises reaction of a compound of the formula:

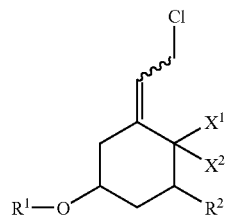

(2)

wherein $X^1$, $X^2$, $R^1$, $R^2$, and the squiggly line are as above, with a binary phase reaction mixture including diphenyl phosphine oxide in an organic solvent, a basic aqueous solution, and a phase transfer catalyst, to obtain the compound of formula 1.

Further aspects and advantages will be apparent to those of ordinary skill in the art from a review of the following detailed description. While the method is susceptible of embodiments in various forms, the description hereafter includes specific embodiments with the understanding that the disclosure is illustrative, and is not intended to limit the invention to the specific embodiments described herein.

DETAILED DESCRIPTION

The invention is an improved process for producing a compound of formula 1 ("Compound 1"). The process involves replacing chlorine in a compound of formula 2 ("Compound 2") by phosphine oxide using a basic aqueous solution to obtain Compound 1. The structures of Compounds 1 and 2 are set forth below.

Compound 1 is a compound of the formula:

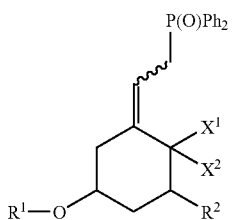

(1)

wherein Ph is phenyl, $X^1$ and $X^2$ are both hydrogen or $X^1$ and $X^2$ taken together are $CH_2$, $R^1$ is a protecting group, $R^2$ is fluorine, hydrogen, or $OR^3$, wherein $R^3$ is a protecting group, and the squiggly line represents a bond that results in the adjacent double bond being in either the E or Z configuration. For clarity, the squiggly line is shorthand for the following two configurations:

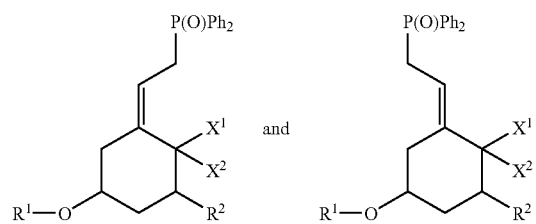

Since Compound 1 can be used in numerous synthetic pathways for producing vitamin D analogs, the bonds between the ring carbons and the $OR^1$ substituent and $R^2$ can be in either the α or β configuration as needed for the final synthesis.

A prior process for preparing compounds similar to Compound 1 has been described in U.S. Pat. No. 6,603,030 ("the '030 patent"). In the '030 patent, a compound similar to Compound 2 is reacted with a salt of diphenylphosphine oxide to form Compound 1. Under anhydrous conditions, a strong base, such as a metal hydride, abstracts a proton from diphenyl phosphine oxide to form a metal salt of diphenyl phosphine oxide, which is stable in anhydrous solvents, such as dimethylformamide. The metal salt then reacts with the halide of Compound 2 via an anionic nucleophilic displacement mechanism to form Compound 1.

In the presently disclosed method, a biphasic system is employed of water and an organic solvent. As such, a salt of the type formed in the '030 patent process cannot be present because it would react with water. Rather, a nucleophilic displacement reaction between the alkyl halide of Compound 2 and diphenyl phosphine oxide occurs in the organic phase, followed by elimination of an HCl molecule effected by a phase transfer catalyst associated with a basic moiety, e.g., tetrabutylammonium hydroxide ($Bu_4NOH$), to form Compound 2. In this example, the base, $Bu_4NOH$, can be formed from the reaction between potassium hydroxide and a tetrabutyl ammonium salt, e.g., $Bu_4NBr$, in the aqueous phase and it moves into the organic phase.

As disclosed herein, Compound 1 is produced by reacting Compound 2 of the formula:

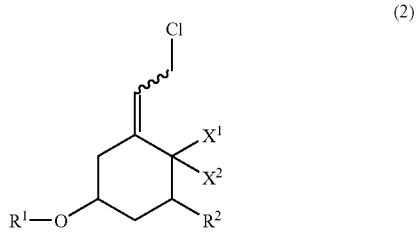

(2)

wherein $X^1$, $X^2$, $R^1$, $R^2$, and the squiggly line are as above, using a binary phase reaction mixture including diphenyl phosphine oxide in an organic solvent, a basic aqueous solution, and a phase transfer catalyst, to obtain the compound of formula 1.

While not wishing to be being bound by theory, it is postulated that in the disclosed method, the allyl chloride of Compound 2 and diphenylphosphine oxide react to form a pentavalent phosphorus intermediate. See, e.g., Moriarty, et al., *Phosphorus, Sulfur, and Silicon*, 109-100:237-240 (1996); Moriarty, et al., *J. Am. Chem.. Soc.*, 112:8575-8577 (1990); and Moriarty, et al., *J. Am. Chem. Soc.*, 113: 9374-9376 (1991) for discussions of pentavalent phosphorus chemistry. The phase transfer catalyst can then chaperone a hydroxide ion from the aqueous phase to the organic phase to react with the pentavalent phosphorus intermediate and form Compound 2. See, e.g., Rabinovitz, et al., *Angew. Chem. Int. Ed. Engl.*, 25:960-970 (1986) for a discussion of phase transfer catalysts.

Any suitable reaction temperature can be used, and it has been found that room temperature reaction conditions produce results in a reasonable amount of time (e.g., about 2 hours). Thus, preferred ranges include about 0° C. to about 40° C., about 10° C. to about 30° C., and at room temperature (e.g., about 20° C. to about 25° C.).

Relatively non-polar solvents in which water has very low solubility are preferably used for the organic phase, for example dichloromethane, toluene, or benzene. Preferred organic solvents for the binary phase reaction mixture will be environmentally-friendly. Suitable examples include diethyl ether, methoxy or ethylphenyl ether, methylpropyl ether, ethylvinyl ether, haloethyl ether, benzyl ether, dibutyl ether, dipropyl ether, butylphenyl ether, butylvinyl ether, cyclohexylvinyl ether, and t-butylmethyl ether. As an environmentally-friendly organic solvent, t-butylmethyl ether is preferred.

The basic compound for the aqueous phase can be an organic base or an inorganic base. Suitable inorganic bases include, but are not limited to, LiOH, NaOH, Cs(OH), $Ca(OH)_2$, $Mg(OH)_2$, $Al(OH)_3$, and potassium hydroxide, with potassium hydroxide being preferred. Suitable organic bases include, but are not limited to, diethyldimethyl ammonium hydroxide, tetramethylammonium hydroxide ($Me_4NOH$), tetraethylammonium hydroxide ($Et_4NOH$), and benzyltrimethylammonium hydroxide ($BnMe_3NOH$) or any tetra alkyl or tetra aryl ammonium hydroxide.

The reaction is performed in the presence of a phase transfer catalyst. Quaternary salts and crown ethers are contemplated. Quaternary salts, including chlorides, bromides, hydrogen sulfates, iodides, ammonium salts, and phosphonium salts, are preferred. Quaternary ammonium and phosphonium salts are preferred.

Quaternary ammonium salts include, but are not limited to, those identified in Table 1 below. Triethylbenzyl chloride and tetra-n-butylammonium bromide are preferred.

TABLE 1

Tetramethylammonium bromide
Tetramethylammonium chloride
Tetramethylammonium hexafluorophosphate
Tetramethylammonium hydroxide pentahydrate
Tetramethylammonium hydroxide
Tetramethylammonium hydroxide
Tetramethylammonium iodide
Tetramethylammonium nitrate
Tetramethylammonium perchlorate
Tetramethylammonium tetrafluoroborate
Triethylmethylammonium chloride
Tetraethylammonium bromide
Tetraethylammonium chloride monohydrate
Tetraethylammonium hydroxide
Tetraethylammonium hydroxide
Tetraethylammonium hydroxide
Tetraethylammonium iodide
Tetraethylammonium nitrate
Tetraethylammonium perchlorate
Tetraethylammonium tetrafluoroborate
Tetraethylammonium p-toluenesulfonate
(1-Hexyl)trimethylammonium bromide
Phenyltrimethylammonium bromide
Phenyltrimethylammonium chloride
Phenyltrimethylammonium iodide
Phenyltrimethylammonium methosulfate
Benzyltrimethylammonium bromide
Benzyltrimethylammonium chloride
Benzyltrimethylammonium hexafluorophosphate
Benzyltrimethylammonium hydroxide
Benzyltrimethylammonium hydroxide,
Benzyltrimethylammonium iodide
(1-Butyl)triethylammonium bromide
(1-Octyl)trimethylammonium bromide
Tetra-n-propylammonium bromide
Tetra-n-propylammonium chloride
Tetra-n-propylammonium hydrogen sulfate
Tetra-n-propylammonium hydroxide
Tetra-n-propylammonium iodide TABLE 1-continued Phenyltriethylammonium iodide
Methyltri-n-butylammonium bromide
Methyltri-n-butylammonium chloride
(1-Decyl)trimethylammonium bromide
Benzyltriethylammonium bromide
Benzyltriethylammonium chloride
Benzyltriethylammonium hydroxide
Benzyltriethylammonium tetrafluoroborate
(1-Dodecyl)trimethylammonium chloride
(1-Dodecyl)trimethylammonium bromide
Benzyltri-n-propylammonium chloride
Tetra-n-butylammonium acetate
Tetra-n-butylammonium acetate,
Tetra-n-butylammonium bromide
Tetra-n-butylammonium chloride
Tetra-n-butylammonium chloride
Tetra-n-butylammonium hexafluorophosphate
Tetra-n-butylammonium hydrogen sulfate
Tetra-n-butylammonium hydroxide
Tetra-n-butylammonium hydroxide
Tetra-n-butylammonium hydroxide
Tetra-n-butylammonium hydroxide
Tetra-n-butylammonium iodide
Tetra-n-butylammonium nitrate
Tetra-n-butylammonium perchlorate,
Tetra-n-butylammonium perchlorate
Tetra-n-butylammonium phosphate
Tetra-n-butylammonium sulfate
Tetra-n-butylammoniumtrifluoromethanesulfate
(1-Tetradecyl)trimethylammonium bromide
(1-Tetradecyl)trimethylammonium chloride
(1-Hexadecyl)trimethylammonium bromide
Ethyl(1-hexadecyl)dimethylammonium
Tetra-n-pentylammonium iodide
Benzyltri-n-butylammonium bromide
Benzyltri-n-butylammonium chloride
Benzyltri-n-butylammonium hydroxide
(1-Hexadecyl)pyridinium bromide monohydrate
(1-Hexadecyl)pyridinium chloride monohydrate
Di-n-decyldimethylammonium bromide
Tetra-n-hexylammonium bromide
Tetra-n-hexylammonium hydrogen sulfate
Tetra-n-hexylammonium iodide
Tetra-n-hexylammonium perchlorate
Di-n-dodecyldimethylammonium bromide
Tetra-n-heptylammonium bromide
Tetra-n-heptylammonium iodide
Tetra-n-octylammonium bromide
Dimethyldistearylammonium chloride
Tetra-n-dodecylammonium iodide
Tetraoctadecylammonium bromide Phosphonium salts include, but are not limited to, bis (triphenylphosphoranilydene)-ammonium chloride, (1-Hexadecyl)tri-n-butylphosphonium bromide, tetra-n-butylphosphonium bromide, tetraphenylphosphonium bromide, tetraphenylphosphonium chloride, tetraphenylphosphonium hexafluoro-antimonate, tetraphenylphosphonium iodide, tetraphenylphosphonium tetrafluoroborate, (triphenylmethyl)triphenylphosphonium chloride.

Compound 2 can be produced by chlorinating a compound of the formula:

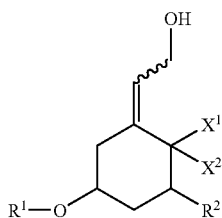

(3)

wherein $X^1$, $X^2$, $R^1$, $R^2$, and the squiggly line are as above, for example by using N-chloro succinimide or a mixture of mesyl chloride/lutidine/lithium chloride or triphosgene.

Compound 2 is obtained from Compound 3 by chlorinating the allylic alcohol of Compound 3 to the allylic chloride in Compound 2. This chlorinating is performed in an organic solvent such as hexane, dichloromethane or dimethylformamide. For each mole of Compound 3, one-half (½) mole or more of triphosgene, two (2) moles or more of N-chlorosuccinimide or a mixture of two (2) moles or more of mesylchloride and four (4) moles or more of lithium chloride can be used as the chlorine source. At least 2 equivalents of an organic base, preferably an aprotic amine base such as pyridine, or preferably triethylamine, should be included. Temperature is not critical and may range between −30° C. and 50° C. A temperature around 0° C. is preferred.

Many species of Compound 3 are known. See, for example, Perlman et al., Novel synthesis of 19-nor-vitamin D compounds, *Tetrahedron Lett.*, 32(52):7663-6 (1991); Courtney et al., Asymmetric synthesis of a key ring A synthon for 1α-hydroxy-19-nor vitamin D, *Tetrahedron Lett.*, 39(21): 3363-3366 (1998); Shiuey et al. Total synthesis of 1α-fluoro-25-hydroxycholecalciferol and -ergocalciferol., *J. Org. Chem.* 55(1):243-7 (1990); Reddy, Synthesis and activity of 3-epi vitamin $D_3$ compounds for use in treatment of disorders involving aberrant activity of hyperproliferative skin, parathyroid, and bone cells, WIPO PCT Publication No. WO 98/51663; Sotojima, Preparation of cyclohexylideneethanol derivatives as intermediates for 1α-hydroxy- and 1α,25-dihydroxyvitamin $D_3$; JP Kokai No. 05279283; Baggiolini et al., Stereoselective total synthesis of 1α,25-dihydroxycholecalciferol, *J. Am. Chem. Soc.*, 104(10):2945-8 (1982). The remaining species of Compound 3 can be produced from these known compounds using procedures known in the art. Such production is well within the skill of the artisan.

In any of the above processes of the invention, $R^1$ can be any appropriate protecting group. The choice of an appropriate protecting group is within the skill of the artisan. For example, suitable protecting groups are described in Wuts et al., *Greene's Protective Groups in Organic Synthesis*, 4th ed., (Wiley Interscience: Hoboken, N.J.) 2007. By hydroxy protecting group is meant any compound for protecting a hydroxy group during a chemical reaction (preferably such that the hydroxy group is easily reinstated), specifically during acidic or basic hydrolysis. A silyl protecting group, such as tert-butyl dimethyl silyl ("TBDMS" or "TBS") is preferred.

$R^2$ can be fluorine, hydrogen, or a protected hydroxyl group. A protected hydroxy group is a group in which oxygen binds to the ring and is protected by a protecting group. As above, the choice of an appropriate protecting group is within the skill of the artisan. For example, suitable protecting groups are described in Wuts et al., *Greene's Protective Groups in Organic Synthesis*, 4th ed., (Wiley Interscience: Hoboken, N.J.) 2007. Preferred protected hydroxy groups include silyl protected hydroxy groups, such as hydroxy protected by TBS. The use of a TBS-protected hydroxy group results in $R^2$ being tert-butyl dimethyl silyl oxide ("TBDMSO"). For any compound used of the invention, $R^1$ and $R^2$ may use the same or different hydroxy protecting groups. In a preferred process, $R^1$ is TBS and $R^2$ is fluorine or TBDMSO.

In another preferred processes of the invention, $R^1$ is TBS, $R^2$ is $OR^3$, and $R^3$ is TBS. In still other preferred processes, $R^1$ is TBS and $R^2$ is fluorine. In yet other preferred processes, $R^1$ is TBS and $R^2$ is hydrogen. In the subject invention, Compounds 1, 2, and 3 can have the $P(O)(Ph)_2$, Cl, and OH, respectively, in either the cis or trans position. In any of these compounds, $R^1$ and $R^2$ may be present above (⟶) or below (⟶) the plane of the cyclohexane ring to which they are attached. Both may be above, both may be below, or one may be above and the other may be below.

EXAMPLES

The following examples are provided for illustration and are not intended to limit the scope of the invention.

Example 1

Preparation of 3S-(3α,5β,Z)-2-2-2-methylene-bis(1,1-dimethylethyl)dimethyl-silyl-oxy-cyclohexylidene-ethyl-diphenyl phosphine oxide

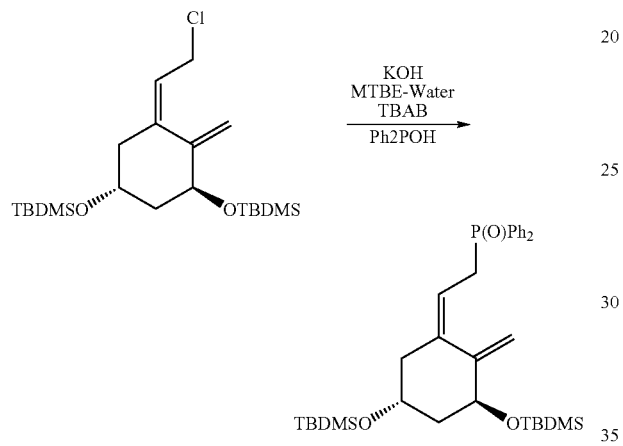

Potassium hydroxide (1.0 g, 17.97 mmole) was dissolved in water (0.5 mL) and was then added to a mixture of tetra-n-butylammonium bromide (TBAB) (1.16 g, 3.59 mmole) as phase transfer catalyst and diphenyl phosphine oxide (2.9 g, 14.37 mmole, prepared from chloro-diphenyl phosphine) in methyl t-butyl ether (MTBE) (40 mL) at room temperature. After stirring for 15 minutes, a solution of the chloro-compound (Z)-(1 S,5R)-1,5-bis-(tert-butyl-dimethyl-silanyloxy)-3-(2-chloro-ethylidene)-2-methylene-cyclohexane (5.0 g, 11.98 mmole) in MTBE (15 mL) was added drop-wise (during 5-10 min.). The reaction mixture was then stirred for 2 hours at room temperature.

Thin Layer Chromatography (TLC) showed only a small amount of starting material (5-10%). The reaction product was diluted with MTBE (50 mL) and water (25 mL). The layers were separated and the organic layer was washed with water (25 mL) and brine (25 mL), dried with anhydrous $Na_2SO_4$, filtered, and concentrated under vacuum. The crude (6.0 g) was purified by column chromatography (EA: Hexane) to give 2.5g (~50%) of the desired phosphine oxide (94% desired by HPLC purity). This material was re-purified by column chromatography (EA: Hexane) to afford 1.7 g of pure material (1.7g, HPLC=96.04%). Identification and purity were verified by $^1$H NMR and HPLC. The remaining fractions were collected and added into the next batch.

Positive results also have been obtained using $Me_4NOH$, $Et_4NOH$ and $BnMe_3NOH$, as bases, each in place of potassium hydroxide.

The foregoing description is given for clearness of understanding only, and no unnecessary limitations should be understood therefrom, as modifications within the scope of the invention may be apparent to those having ordinary skill in the art.

Throughout the specification, where methods are described as including steps, components, or materials, it is contemplated that the compositions can also consist essentially of, or consist of, any combination of the recited steps, components or materials, unless described otherwise.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A process for producing a compound of formula (1):

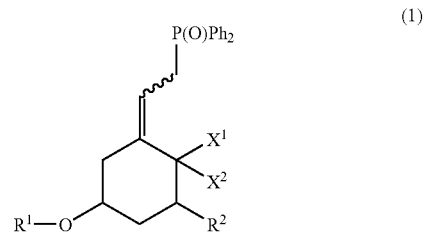

comprising reacting a compound of formula (2):

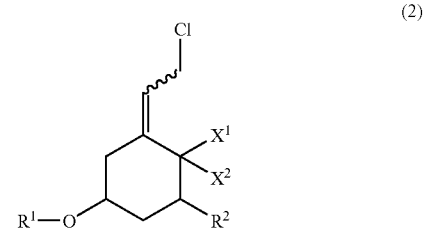

with diphenyl phosphine oxide using a binary phase reaction mixture comprising diphenyl phosphine oxide in an organic solvent, a basic aqueous solution, and a phase transfer catalyst selected from the group consisting of a quaternary salt, a crown ether, and a mixture thereof, to obtain the compound of formula 1, wherein Ph is phenyl, $X^1$ and $X^2$ are both hydrogen or $X^1$ and $X^2$ taken together are $CH_2$, $R^1$ is a protecting group, $R^2$ is fluorine, hydrogen, or $OR^3$, wherein $R^3$ is a protecting group, and the squiggly line represents a bond that results in the adjacent double bond being in either the E or Z configuration.

2. The process claim 1 wherein $R^1$ is a silyl protecting group.

3. The process of claim 2, wherein $R^1$ is a tert-butyl dimethyl silyl group.

4. The process of claim 1, wherein $R^2$ is fluorine.

5. The process of claim 1, wherein $R^2$ is tert-butyl dimethyl silyl oxide.

6. The process of claim 1, wherein $R^2$ is fluorine or tert-butyl dimethyl silyl oxide.

7. The process of claim 1, wherein $X^1$ and $X^2$ taken together are $CH_2$.

8. The process of claim 1, wherein the organic solvent is selected from the group consisting of diethyl ether, methoxyphenyl ether, ethylphenyl ether, methylpropyl ether, ethylvinyl ether, a haloethyl ether, benzyl ether, dibutyl ether, dipropyl ether, butylphenyl ether, butylvinyl ether, cyclohexylvinyl ether, t-butylmethyl ether, and mixtures thereof.

9. The process of claim 1, wherein the organic solvent comprises t-butylmethyl ether.

10. The process of claim 1, wherein the basic aqueous solution comprises an inorganic base.

11. The process of claim 10, wherein the inorganic base is selected from the group consisting of lithium hydroxide, sodium hydroxide, cesium hydroxide, calcium hydroxide, magnesium hydroxide, aluminum hydroxide, potassium hydroxide, and mixtures thereof.

12. The process of claim 10, wherein the inorganic base is potassium hydroxide.

13. The process of claim 1, wherein the basic aqueous solution comprises an organic base.

14. The process of claim 13, wherein the organic base is selected from the group consisting of $Me_4NOH$, $Et_4NOH$, $BnMe_3NOH$, and mixtures thereof.

15. The process of claim 1, wherein the phase transfer catalyst comprises one or more quaternary ammonium salts.

16. The process of claim 15, wherein the phase transfer catalyst comprises tetra-n-butylammonium bromide.

17. The process of claim 1, wherein the reaction is performed at a temperature in a range of about 0° C. to about 40° C.

18. The process of claim 17, wherein the reaction is performed at a temperature in a range of about 10° C. to about 30° C.

19. The process of claim 18, wherein the reaction is performed at room temperature.

* * * * *